United States Patent [19]

Cullis et al.

[11] Patent Number: 4,975,282

[45] Date of Patent: Dec. 4, 1990

[54] MULTILAMELLAR LIPOSOMES HAVING IMPROVED TRAPPING EFFICIENCIES

[75] Inventors: Pieter R. Cullis; Marcel B. Bally; Michael J. Hope, all of Vancouver, Canada; Andrew S. Janoff, Yardley, Pa.; Lawrence D. Mayer, Vancouver, Canada

[73] Assignee: The Liposome Company, Inc., Princeton, N.J.

[21] Appl. No.: 122,613

[22] Filed: Nov. 17, 1987

Related U.S. Application Data

[63] Continuation of Ser. No. 800,545, Nov. 21, 1985, abandoned, which is a continuation-in-part of Ser. No. 752,423, Jul. 5, 1985, abandoned, which is a continuation-in-part of Ser. No. 749,161, Jun. 26, 1985, abandoned.

[51] Int. Cl.$^5$ .............................................. A61K 37/22
[52] U.S. Cl. .................................................. 424/450
[58] Field of Search .......................... 424/16, 38, 450

[56] References Cited

U.S. PATENT DOCUMENTS

| 4,016,100 | 4/1977 | Suzuki et al. | 252/316 |
|---|---|---|---|
| 4,394,372 | 7/1983 | Taylor | 424/85 |
| 4,397,846 | 8/1983 | Weiner et al. | 514/104 |
| 4,515,736 | 5/1985 | Deamer | 424/38 |
| 4,529,561 | 7/1985 | Hunt et al. | 264/4.3 |
| 4,532,089 | 7/1985 | MacDonald | 424/38 |

OTHER PUBLICATIONS

Ohsawa et al., Chem. Pharm. Bull., 33(7) 2916–2923(1985), "Evaluation of a New Liposome Preparation Technique, The Freeze-Thawing Method, Using L-Asparaginase as a Model Drug".
Ohsawa et al., Chem. Pharm. Bull., 1985, 33 (9):3945–3952, "Improvement of Encapsulation Efficiency of Water-Soluble Drugs in Liposomes Formed by the Freeze-Thawing Method".
Ohsawa et al., Chem. Pharm. Bull., 1985, 33(11):5013–5022, "Fate of Lipid and Encapsulated Drug After Intramuscular Administration of Liposomes Prepared by the Freeze-Thawing Method in Rats".
Oku et al., Biochem., 1983, 22(4):855–863, "Differential Effects of Alkali Metal Chlorides on Formation of Giant Liposomes by Freezing and Thawing and Dialysis".
Gruner et al., Novel Multilayered Lipid Vesicles Comparison of Physical Characteristics of Multilamellar Liposomes and Stable Plurilamellar Vesicles, 1985, Biochem. 24, pp. 2833–2842.
Kirby et al., A Simple Procedure for Preparing Liposomes Capable of High Encapsulation Efficiency Under Mild Conditions, 1984 In: *Liposome Technology*, Gregoriadis G., Ed. CRC Press, Inc., vol. 1, pp. 19–27.
Pick, U. Liposomes with a Large Trapping Capacity Prepared by Freezing and Thawing of Sonicated Phospholipid Mixtures, 1981, Arch. Biochem. Biophys. 212 (1), pp. 186–194.
Westman et al., Charge and pH Dependent Drug Binding to Model Membranes, 1982, BBA, pp. 315–328.
Strauss, G., Freezing and Thawing of Liposome Suspensions, 1984, In: *Liposome Technology*, Gregoriadis, G., Ed., CRC Press, Inc., vol. 1, pp. 197–219.
Olson et al., Preparation of Liposomes of Defined Size Distribution by Extrusion Through Polycarbonate Membranes, 1979, BBA 557, pp. 9–23.

*Primary Examiner*—Douglas W. Robinson
*Assistant Examiner*—Raymond J. Henley, III
*Attorney, Agent, or Firm*—Allen Bloom; Catherine L. Kurtz

[57] ABSTRACT

A multilamellar vesicle dispersed in an aqueous phase comprising an aqueous medium, a lipid concentration of at least about 50 mg/ml and a trapping efficiency of at least about 40 percent. The vesicle can be prepared by dispersing the lipid in an aqueous phase to form a multilamellar vesicle, rapidly freezing the multilamellar vesicle to obtain a frozen lipid-aqueous medium mixture, and warming the mixture to obtain a frozen and thawed multilamellar vesicle dispersed in an aqueous phase.

28 Claims, 8 Drawing Sheets

A

B

MULTILAMELLAR LIPOSOMES HAVING IMPROVED TRAPPING EFFICIENCIES

This is a continuation of co-pending application Ser. No. 06/800,545 filed on Nov. 21, 1985, now abandoned which is a continuation-in-part of 06/752,423 July 5, 1985, now abandoned which is a continuation-in-part of Ser. No. 06/749,161, June 26, 1985, now abandoned.

BACKGROUND OF THE INVENTION

The present invention is directed to liposomes. More particularly, the present invention is directed to multilamellar vesicles having improved trapping efficiency and equilibrium transbilayer solute distribution.

Liposomes of the type which are multilamellar vesicles (MLV's) are usually formed by mechanical dispersion of dried lipid in an aqueous buffer. It is commonly assumed that this procedure results in an equilibrium interlamellar distribution of solutes present in the buffer. However, it has been demonstrated that the trapped buffer may have reduced solute concentrations resulting in osmotic imbalances between exterior and interior environments. Gruner et al., *Biochemistry*, 24, 2833–2842 (1985). These osmotic imbalances can lead to membrane potentials, transbilayer pH gradients and deformations due to osmotic forces. Equilibrium solute distributions can be achieved by techniques involving dispersion of the lipid in mixtures of organic solvent and aqueous buffer, where the organic solvent is subsequently removed under reduced pressure.

Alternative procedures have been described in U.S. Pat. No. 4,522,803 and copending U.S. patent applications Ser. Nos. 476,496 and 521,176, and incorporated herein by reference, to prepare liposomes having properties different than MLV's.

The low trapping volume and trapping efficiency of MLV systems have presented difficulties in employing these systems in applications such as drug delivery. As a result, alternative procedures have been developed to prepare liposomal systems which involve the use of organic solvents or detergents as solubilizing agents. Organic solvents and detergents are undesirable ingredients in drug delivery systems.

It would, therefore, be desirable to obtain a multilamellar vesicle having high trapping efficiency, high trapped volumes and equilibrium transbilayer solute distribution prepared in the absence of organic solvents or detergents.

SUMMARY OF THE INVENTION

We have prepared a new multilamellar vesicle dispersed in an aqueous phase comprising an aqueous medium, a trapping efficiency of at least 40 percent and a lipid concentration of at least about 50 mg/ml. Preferably, the trapping efficiency is at least about 50 percent and the lipid concentration is at least about 100 mg/ml, more preferably between about 100 and 1000 mg/ml, and still more preferably between about 100 and 400 mg/ml.

The vesicles of the present invention have an interlamellar equal solute distribution. The vesicle can contain a bioactive agent. The lipid can comprise phospholipid such as phosphatidylcholine, and may additionally comprise a sterol such as cholesterol. The vesicle can be concentrated by removal of all or part of the aqueous phase.

The multilamellar vesicles of the present invention can be prepared by dispersing (a) a lipid in an aqueous phase to form a multilamellar vesicle, (b) rapidly cooling the multilamellar vesicle to obtain a frozen lipid-aqueous medium mixture, and (c) warming the mixture. The rapid cooling step preferably employed liquid nitrogen. Preferably, steps (b) and (c) are performed at least about five times.

In addition, the resulting multilamellar vesicles of the present invention can be filtered through polycarbonate filters to obtain a resulting vesicle dispersed in an aqueous phase comprising a lipid concentration of at least about 5 mg/ml of aqueous phase, a mean diameter of less than about 100 nanometers and a trapping efficiency of at least about 10%. Preferably the lipid concentration is at least about 100 mg/ml, more preferably about 100–400 mg/ml. The trapping efficiency is preferably about 40%. Preferably the resulting vesicles have a uniform size distribution.

DETAILED DESCRIPTION OF THE INVENTION

Figure 1:
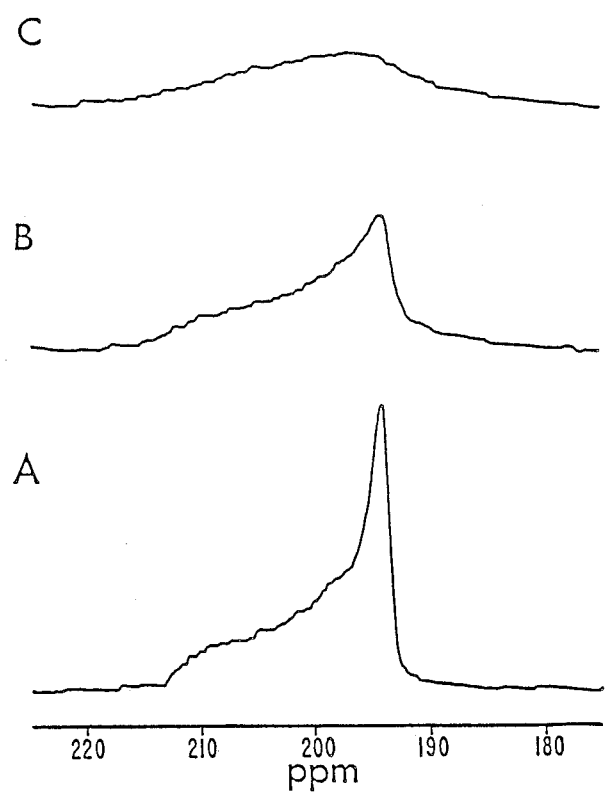
FIG. 1 is an NMR spectrum of (A) an MLV in the absence of $Mn^{2+}$, (b) an MLV prepared in the presence of 0.5 mM $Mn^{2+}$.

The following definitions will be employed:

liposome—any structure composed of lipid bilayers that enclose a volume.

multilamellar vesicles (MLVs)—liposomes containing multiple lipid bilayers forming two or more shells.

FATMLV—A MLV which has been subject to at least one freeze-thaw cycle.

lipid—an agent exhibiting amphipathic characteristics causing it to spontaneously adopt an organized structure in water wherein the hydrophobic portion of the molecule is sequestered away from the aqueous phase.

freeze-thaw-cycle—cooling a liposome below the freezing point of the aqueous solvent contained within the liposome, then warming to a temperature whereby the aqueous medium or phase is melted.

trapping efficiency or encapsulation efficiency—the fraction of an aqueous phase sequestered by liposome bilayers when a lipid is dispersed in the aqueous phase; given as the percent of the original volume of the aqueous phase.

captured volume or trapped volume—the volume enclosed by a given amount of lipid with units of liters entrapped per mole of total lipid.

lipid concentration—the amount of lipid added per ml of aqueous phase; the units are generally mg/ml.

Multilamellar vesicles (MLV's) can be prepared by a number of methods. In one process, one or more selected lipids are deposited on the inside walls of a suitable vessel by dissolving the lipids in an organic solvent such as chloroform and then evaporating the organic solvent, adding an aqueous phase which is to be encapsulated to the vessel, allowing the aqueous phase to hydrate the lipid, and mechanically agitating, for example, swirling or vortexing, the resulting lipid suspension to produce the desired liposomes.

Alternatively, one or more selected lipids can be dispersed by employing mechanical agitation in an aqueous phase to produce MLV's. The process requires about 1-10 minutes at a temperature above the gel/liquid crystalline transition temperature.

The organic solvent can contain a bioactive agent such as a drug, preferably a bioactive agent which is both soluble in the organic solvent and is lipophilic.

The aqueous medium is that enclosed by lipid bilayers. Generally the aqueous medium will have the same constituents as the aqueous phase, although the amounts may be different. Although the following discussion is directed to an aqueous medium, it clearly also applies to the aqueous phase. The aqueous medium can be for example, water or water containing dissolved salt or buffer. The aqueous medium may contain a bioactive agent, preferably a bioactive agent which is water soluble. Water soluble bioactive agents which can be incorporated into FATMLV's of the present invention include antibacterial aminoglycosides such as tobramycin. Pilocarpine can be incorporated for ocular administration for treating glaucoma.

In the MLV the bioactive agent generally partitions between the aqueous and lipid portions of the liposome depending on the agent's lipophilic and hydrophilic character.

In addition, the MLV's produced by the procedures previously described have low trapped volumes and corresponding low trapping efficiencies, which causes the loss of valuable solutes in the aqueous solvent and the added cost of recycling the untrapped aqueous phase.

The lipids which can be employed in the present invention include cholesteryl hemisuccinate and salts thereof, tocopheryl hemisuccinate and salts thereof, a glycolipid, a phospholipid such as phosphatidylcholine (PC), phosphatidylethanolamine (PE), phosphatidylserine (PS), phosphatidylglycerol (PG), phosphatidic acid (PA), phosphatatidylinositol (PI), sphingomylin (SPM), and the like, alone or in combination. The phospholipids can be synthetic or derived from natural sources such as egg or soy. Sterols such as cholesterol can be combined with the phospholipids. The phospholipids employed and the amount of sterol present depends on a number of factors such as lipophilicity of any added bioactive agent and the required properties of the liposome. These factors are well known to those skilled in the art.

The lipid concentration for the present invention is at least about 50 mg/ml. At lower concentrations, multilamellar vesicles of the present invention having a high trapping efficiency are difficult or impossible to form. A preferred lipid concentration is between about 100 and 1000 mg/ml, more preferably 100-600 mg/ml, and still more preferably 100-400 mg/ml.

A high trapping efficiency results in a large fraction of the aqueous phase being entrapped in the liposome. In the present invention, the liposomes have a trapped efficiency of at least about 40 percent, preferably at least 50 percent and, more preferably about 50-90 percent. Generally, a lipid concentration of at least about 100 mg/ml is needed to obtain a trapping efficiency of at least about 50 percent.

The dispersed lipid mixture results in predominately MLV's. These MLV's have been shown to be in osmotic imbalance when a solute is present in the aqueous medium prior to addition of the lipid. For example, when $Mn^{2+}$ ion from $MnCl_2$ is present in an aqueous buffer, non-equilibrium transmembrane distributions of the paramagnetic $Mn^{2+}$ ion in the MLV's can be observed by NMR spectroscopy. $Mn^{2+}$ is a "broadening" agent which quenches the $^{31}P$ NMR signal arising from phospholipids with which the ion comes in proximity. When there are asymmetric tribilayer concentrations of $Mn^{2+}$ in the MLV, the $^{31}P$ NMR resomme arising from the phospholipids on either side of the bilayers are not equally quenched.

The freeze-thaw cycle of the present invention requires rapid freezing of the dispersed lipid medium mixture and then warming the frozen mixture in a constant temperature bath, to a temperature which will cause the aqueous phase to melt. The temperature employed is generally above the transition temperature for the gel-liquid crystalline transition. A constant temperature bath of about 25°-50° C., preferably about 40° C., is generally effective.

Liquid nitrogen baths have been found to be particularly effective for the freezing step. A comparison was made of the FATMLV's prepared by placing the mixture in dry ice/ethanol and liquid nitrogen baths. For FATMLV's prepared by freezing liquid nitrogen, the trapping efficiency and the trapped volume was at least about 1.5-fold greater then when dry ice/ethanol was employed. At higher lipid concentrations, trapping efficiencies at least four-fold greater can be achieved. FATMLV's prepared using a dry ice/ethanol bath do not have the properties of those of the present invention. Strauss, "Freezing and Thawing of Liposome Suspensions," in Liposome Technology, Ed. G. Gregoriadis, Chapter 15, CRC Press, Inc., Boca Raton, FL, 1984, discusses the rapid vs. slow cooling of liposome preparations and the relevant portions are incorporated herein by reference.

The number of freeze-thaw cycles affects the properties of the resulting FATMLV. Generally, three or more freeze-thaw cycles are required to obtain an equilibrium interlamellar osmotic balance. The balance can be observed by following the effect of the number of freeze-thaw cycles upon the distribution of $Mn^{2+}$ as measured by $^{31}P$ NMR when the FATMLV includes phospholipid-containing bilayers.

When a lipid containing phospholipid solubilized in an aqueous phase by means of a detergent such as Triton X-100, the $^{31}P$ NMR spectrum in the presence of $Mn^{2+}$ shows all the phosphorous to be equally quenched. Essentially the same spectrum is observed for a FATMLV after three cycles.

About five freeze-thaw cycles in liquid nitrogen and a 40° C. constant temperature bath, result in FATMLV's of the present invention. After five freeze-thaw cycles the morphology of the FATMLV changes. Before freeze-thawing, the MLV'S exhibit the tightly packed "onion skin" arrangements of concentric bilayers normally associated with multilamellar liposomes. After five freeze-thaw cycles, a new structure is observed by freeze-fraction electron micrographs. The interlamellar spacing is increased by up to about five fold and closed lamellar systems can be intercalated between bilayers. The tightly packed arrangement is substantially absent.

The FATMLV's after at least about five cycles have significantly greater trapped volume and trapping efficiencies. The trapped volume per umol phospholipid can be determined using $^{22}Na^+$ as an aqueous marker. At 100 mg/ml phosphatidylcholine, more than an order of magnitude increase in trapped volume is observed after five freeze-thaw cycles compared to non-freeze-thawed MLV's. After about eight freeze-thaw cycles additional cycles do not result in any further significant changes in trapped volume.

The freeze-thaw protocol of the present invention is effective for various lipid compositions. For example, for a lipid whose components are egg PC containing between 0 and 50 mole percent cholesterol, substantially the same results with regard to trapped volume were obtained after five freeze-thaw cycles utilizing liquid nitrogen and 40° C. water constant temperature bath.

The fraction of lipid in the outer bilayer in FATMLV's of the present invention is less than about 35 percent. When the lipid is egg PC at a lipid concentration of 50 mg/ml the fraction of lipid in the outer bilayer is about 32-34 percent. The fraction of lipid in the outer bilayer decreases with increasing lipid concentration, but is generally larger than that of MLV's or FATMLV's of the prior art. For egg PC (100 mg/ml) the outer bilayer fraction is about 26-30 percent, 200 mg/ml is about 13-17 percent, and 400 mg/ml is about 13-17 percent. Comparisons should be made for the same ingredients and formulations.

The aqueous phase of the dispersions of the present invention vesicle can be removed to form a concentrated FATMLV dispersion. Methods of removal include diahysis, centrifugation, dehydration and lyophilyation. Dehydration is described in a copending application filed June 26, 1985, M.B. Bally et. al., "Encapslation of Antineoplastic Agents in Liposomes," Ser. No. 749,161 and in a copending application filed July 26, 1985, A.S. Janoff et al., "Dehydrated Liposomes", Ser. No. 759,419, relevant portions of which are incorporated herein by reference.

Variable size vesicles can be prepared by a rapid extrusion technique where lipid dispersions are passed under moderate pressure, e.g., nitrogen at pressures up to about 800 psi, through polycarbonate filters whose pore size can be varied from 30-800 nm or more. Methods relating to rapid extrusion techniques through polycarbonate filters and the use of the methods to obtain liposomes of uniform size distribution are described in the following copending application, relevant portions of which are inforporate herein by reference: Cullis et al., Ser. No. 22,690, filed June 20, 1984; Cullis et al., Ser. No. 622,502, filed June 20, 1984; and Cullis et al., "Extrusion Technique for Producing Unilamellar Vesicles", filed Oct. 16, 1985, Docket No. LIP-101 Div. Unilamellar vesicles with a large, e.g., (151 nm) mean diameter can be produced if FATMLV's of the present invention are passed through 200 nm pore size filters. This freeze-thaw process also increased the aqueous trapped volume of vesicles 1.5 to 3.0 times when filters with pore sizes ranging from 100 to 400 nm were utilized. Increasing the lipid concentration to 400 mg/ml of aqueous buffer for these systems increased the trapping efficiency levels to 80 and 50 percent for vesicle produced employing 400 and 100 nm pore size filters, respectively. Freeze fracture electron microscopy revealed that vesicles produced at the very high lipid concentrations exhibited negligble alterations in size distribution or extent of multilamellarity as compared to systems produced at lower lipid levels. These results suggest that the freeze-thaw extrusion protocol offers a very general and versatile method for producing vesicles of variable sizes and has several advantages that were unavailable with previous procedures. Sized vesicles containing drugs or other bioactive agents are useful for treating illnesses in mammals including humans. For example, sized vesicles containing pilocarpine may be used to treat glaucoma and those containing tobramycin have reduced toxicity.

A variety of unilamellar and multilamellar vesicles of differing sizes can be generated by extrusion of MLV's through polycarbonate filters with different pore sizes. It is convenient to introduce the general term "VET's" to indicate "vesicles by extrusion techniques" with a numerical subscript to indicate the pore size employed. Thus a $VET_{50}$ system indicates vesicles extruded through filters with 50 nm pore size whereas a $VET_{400}$ system indicates extrusion through 400 nm pore size filters. Once the lamellarity and size of these systems has been determined, this nomenclature can be further refined to indicate the large or small character of unilamellar systems or the multilamellarity of other (e.g., large unilamellar vesicles by extrusion through 100 nm filters—$LUVET_{100}$'s; small unilamellar vesicles by extrusion through 50 nm filters—$SUVET_{50}$'s; or multilamellar vesicles obtained by extrusion through 400 nm filters—$MLVET_{400}$'s). An arbitrary decision to designate unilamellar systems extruded through 100 nm or larger pores as "large" has been made, whereas systems extruded through 50 nm or smaller pores are indicated as "small".

Figure 6A:
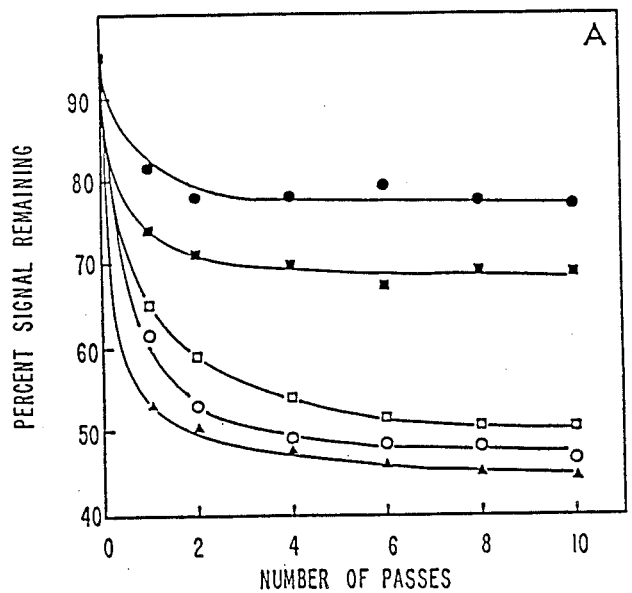
FIG. 6 is a graph of percent $^{31}P$-NMR signal intensity remaining after $Mn^{2+}$ addition for MLVs (A) and FATMLVs (B) passed through polycarbonate filters of defined pore sizes. MLV's and FATMLV's were prepared at 100 mg egg phosphatidyl choline/ml as described in Example 1. $^{31}$Phosporus-NMR signal intensities were determined before and after addition of $Mn^{2+}$ (final concentration=5mM) for vesicles passed the indicated number of times through 400 (◉), 200 (■), 100 (□), 50 (o) and 30 (▲) nm pore size filters.

The influence of external $Mn^{2+}$ on the $^{31}P$ NMP signal intensity of EPC MLV systems (100 mg/ml) extruded through polycarbonate filters with pore sizes in the range 30 nm to 400 nm is illustrated in FIG. 6A. The signal intensity of the $VET_{100}$ systems decreases to 50%, indicating unilamellar character, after 8 passes through two stacked filters. Only 4 passes were found to be required to obtain predominantly unilamellar character when the lipid concentration is about 50 mg/ml or less. The $VET_{50}$ and $VET_{30}$ systems obtained on extrusion through the 50 and 30 nm pore size filters exhibit residual $^{31}P$ NMR intensities of 48% and 44% respectively (after 8 passes) consistent with a unilamellar population of smaller vesicles.

The MLV systems extruded through the 200 nm and 400 nm filters retain multilamellar character as the residual $^{31}$P NMR signal intensities are 70 and 78% respectively. If it is assumed that the multilamellar vesicle population contain only two bilayers which are tightly packed (e.g., separated by 10 nm or less), then this would indicate that approximately 20% of the VET$_{200}$ systems are unilamellar and approximately 80% bilamellar. If the average number of lamellar is more than two, the proportion of unilamellar vesicle will be higher. Similar calculations for the VET$_{400}$ systems are consistent with nearly all the vesicles exhibiting bilamellar character, or with a small proportion of unilamellar vesicles which will increase for higher proportions of multilamellar vesicles with three or more bilayers.

Figure 6B:
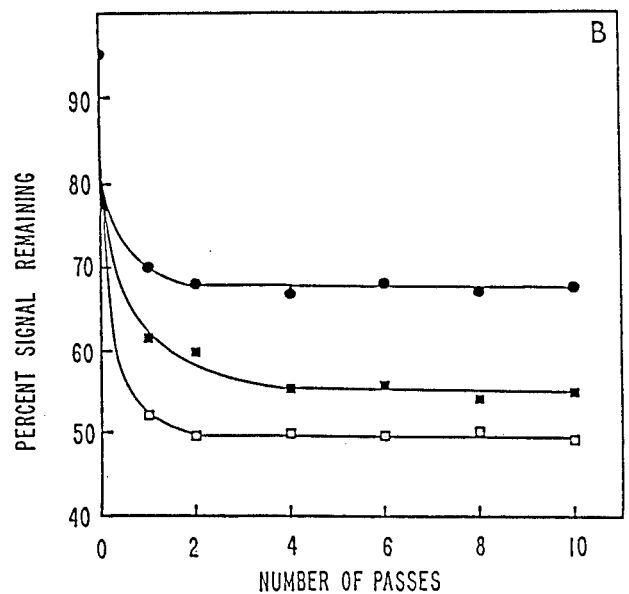

FATMLVs exhibit significantly larger interlamellar spacings and much larger trapped volumes. It may therefore be expected that VET$_{400}$ and VET$_{200}$ systems prepared from FATMLV's should exhibit somewhat higher unilamellar character due to the reduced fraction of tightly packed lamellae in the FATMLV precursors. This appears to be the case as illustrated in FIG. 6B, where it is shown that the residual $^{31}$P NMR intensities (after addition of $Mn^{2+}$) for the VET$_{400}$ and VET$_{200}$ systems are 68% and 56% respectively. This would correspond to an average of approximately 20% unilamellae and 80% containing two (tightly packed) lamellae for the VET$_{400}$ systems and substantial population of unilamellar vesicles (at least 75%) for the VET$_{200}$ systems when prepared from FATMLV's. It may also be noted that fewer passes are required to generate the unilamellar LUVET$_{100}$ system from FATMLV's than from non-freeze thawed MLV's. Similar effects were observed for the SUVET$_{50}$ and SUVET$_{30}$ preparations.

Figure 7:
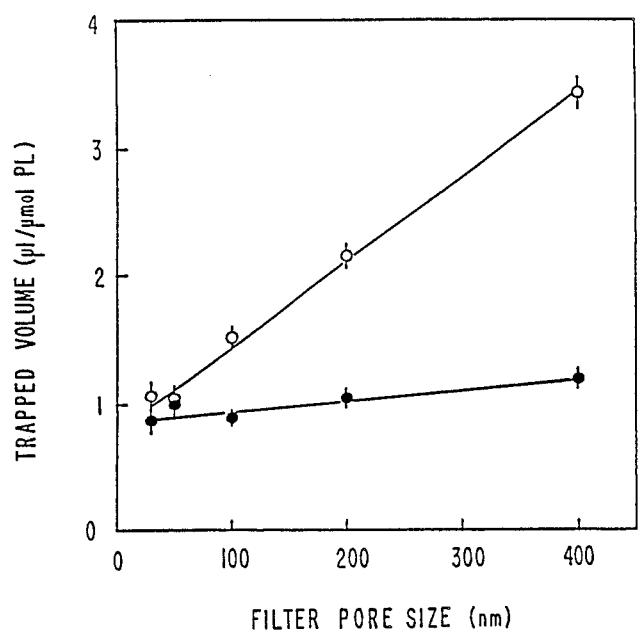
FIG. 7 is a graph of aqueous trapped volumes of MLVs (•) and FATMLVs (o) passed 20 times through polycarbonate filters of the indicated pore size. Vesicles were prepared at 100 mg lipid/ml of buffer containing $^{14}C$-inulin. The error bars represent the standard deviation determined from 3 samples.

Assuming a similar size distribution, the increased unilamellar character of the VET$_{400}$ and VET$_{200}$ systems prepared from FATMLV's suggests that the trapped volume (expressed as liters trapped/ mol phospholipid) of freeze-thawed, sized vesicles should be significantly increased. That this is the case is illustrated in FIG. 7, where the trapped volume of the vesicles prepared from FATMLV's increases from 1 l/mol to 3.6 l/ mol phospholipid as the pore size is increased from 30 to 400 nm. This contrasts strongly with the trapped volumes of the VET's prepared from MLV precursors, which increase by 20% or less for the same range of pore sizes. It is interesting to note that whereas the trapped volumes of the SUVET$_{30}$ and SUVET$_{50}$ vesicles are the same for FATMLV and MLV precursors, the trapped volumes of the LUVET$_{100}$ systems increase by 50% (to 1.5 l/mol) when FATMLV's are employed. Comparable results were observed when $^{14}$C-inulin was used as the aqueous trap marker rather than $^{22}$Na. Given that the $^{31}$P NMR data indicate unilamellar character for FATMLV and MLV systems extruded through filters with 100 nm pore size or less, it would not be expected that the trapped volumes observed should be sensitive to the freeze-thaw procedure.

The size distributions calculated by the procedure of van Venetie et al (see Methods and Materials) are given in Table 3 and reveal relatively homogeneous vesicle populations whose mean sizes are either somewhat smaller than the filter pore size (e.g., the VET$_{400}$ and VET$_{200}$ systems) or of the same size or larger than the filter pore size (e.g., the SUVET$_{50}$ and SUVET$_{30}$ systems). The size of the VET$_{200}$ vesicles is likely related do the fact that the actual pore sizes of the Nucleopore membranes are approximately 10% smaller than specified, whereas the sizes of the SUVET$_{50}$ and SUVET$_{30}$ systems may reflect a limiting size of the VET systems.

The vesicle sizes determined by light scattering techniques are also given in Table 3.

The results indicate that homogeneously-sized vesicles of SUV, LUV or MLV character can be readily generated by extruding MLV's or FATMLV's through polycarbonate filters of appropriate pore size.

Figure 8:
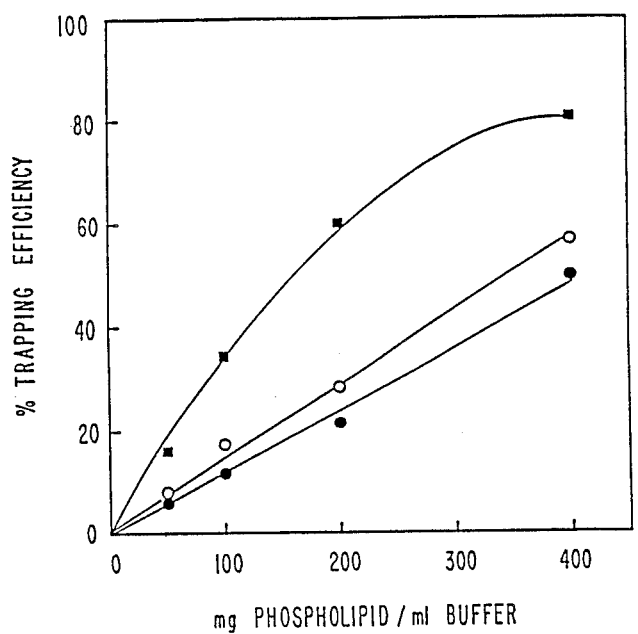
FIG. 8 is a graph of percent trapping efficiency of FATMLVs passed through 400 (■), 100 (◉) and 50 (o) nm pore size filters as a function of phospholipid concentration. Vesicles were prepared in the presence of $^{22}Na$ as an aqueous marker. The values given represent the amount of $^{22}Na$ remaining associated with the vesicles after removal of free $^{22}Na$ relative to the total amount of $^{22}Na$ in the initial lipid dispersion.

In FIG. 8, trapping efficiencies of 81%, 56% and 50% are obtained for FATMLV's (prepared at 400 mg/ml) extruded through 400 nm, 100 nm and 50 nm filters respectively. These trapping efficiencies are clearly remarkable, particularly for the smaller VET$_{100}$ and VET$_{50}$ systems. Freeze-fracture micrographs of VET$_{100}$ systems obtained at 400 mg/ml and then diluted to 100 mg/ml show that the size distribution is similar to that observed for the LUVET$_{100}$ systems prepared at 100 mg/ml and the low frequency of cross-fractures supports a unilamellar character.

When injected directly into the bloodstream, small vesicles are generally less leaky and remain in the blood for a longer time than larger systems.

MATERIALS AND METHODS

Egg phosphatidylcholine (EPC) was purified from hen egg yolks according to established procedures (see Singleton et. al., *Journal of the American Oil Chemical Society* 42, 53 (1965) ) and was chromatographically pure. $^{22}$NaCl and $^{14}$C-inulin were obtained from NEN Canada, Quebec.

Extrusion of the MLV or FATMLV preparations through two (stacked) polycarbonate filters of the various pore sizes (30–400 nm) was performed employing nitrogen pressures of up to 800 psi. $^{31}$P NMR spectra of egg PC liposomes were obtained employing a Bruker WP-200 spectrometer operating at 81.0 MHz. Free induction decays corresponding to 1000 transients were accumulated utilizing 15 usec 90° radio frequency pulse, gated proton decoupling and a 20 KHz sweep width. An exponential multiplication corresponding to a 40 Hz line broadening was applied prior to Fourier transformation. Signal intensities were determined by cutting and weighing spectra.

The size distributions of the extruded liposomal systems were determined by freeze-fracture microscopy and quasi-elastic light scattering. Vesicle preparations to be used for freeze-fracture were mixed with glycerol (25% by volume) and frozen in a Freon slush. Samples were fractured and replicas obtained employing a Balzers BAF 400D apparatus, and micrographs of the replicas were produced using a Phillips' 400 electron microscope. Vesicle size distributions were estimated by measuring the diameter of fractured vesicles exhibiting 50% shadowing according to the procedure of van Venetie et al, *Journal of Microscopy*, 118, 401–408 (1980). Size distributions determined by quasi-elastic light scattering (QELS) analysis was performed utilizing a Nicomp Model 200 Laser Particle Sizer with a 5 milliwatt Helium-Neon Laser at an exciting wavelength of 632.8 nm. QELS, also referred to as dynamic light scattering or photon correlation spectroscopy, employs digital autocorrelation to analyze the fluctuations in scattered light intensity generated by the diffusion of vesicles in solution. The measured diffusion coefficient is used to obtain the average hydrodynamic radius and hence the mean diameter of the vesicles.

Vesicle trapped volumes were determined as follows: Phospholipid vesicles were hydrated and dispersed in the presence of tracer amounts of $^{22}$NaCl or $^{14}$C-inulin (1 uCi/ml). Subsequent to the extrusion process the vesicles were diluted to 100 mg/ml (when necessary) and passed down a Sephadex 650 or Ultrogel (LKB AcA-34) column to remove untrapped $^{22}$Na+ or $^{14}$C-inulin, respectively Aliquots of the vesicle-containing fraction were assayed for lipid phosphorus (15) and monitored for $^{22}$Na+ utilizing a Beckman 8000 gamma counter or $^{14}$C-inulin using a Phillips' PW-4700 liquid scintillation counter. Trapped volumes were calculated and expressed as ul of aqueous trapped volume per umol of phospholipid. Trapping efficiencies were calculated as the dpm/umol phospholipid after gel filtration divided by the dpm/umol phospholipid before the gel filtration step.

EXAMPLE 1

FIGS. 1 (A) and (B) show the 81.0 MHz $^{31}$P NMR spectra of egg phosphatidylcholine multilamellar vesicles of the prior art dispersed (A) in the absence of $Mn^{2+}$ and (B) in the presence of 0.5 mM $Mn^{2+}$. The spectra of (C) was obtained from the MLV's dispersed in the presence of 0.5 mM $Mn^{2+}$ which were subsequently subjected to 5 freeze-thaw cycles employing liquid nitrogen and a 40° C. water constant temperature bath in order to obtain vesicles of the present invention. The phosphatidylcholine was isolated from egg yolks employing standard procedures and was more than 99% pure as indicated by thin layer chromatography. The MLV's were prepared by adding 2 ml of buffer (150 mM sodium chloride, 20 mM Hepes, pH 7.5) to 200 mg of lipid. This dispersion was vortexed intermittently (2 min. vortexing, 3 min. interval) over 20 min. The $^{31}$P NMR spectra were collected at 20° C. employing a Bruker WP 200 spectrometer utilizing a 20 KHz sweep width, 2 sec interpulse delay and broad band proton decoupling.

EXAMPLE 2

Figure 2:
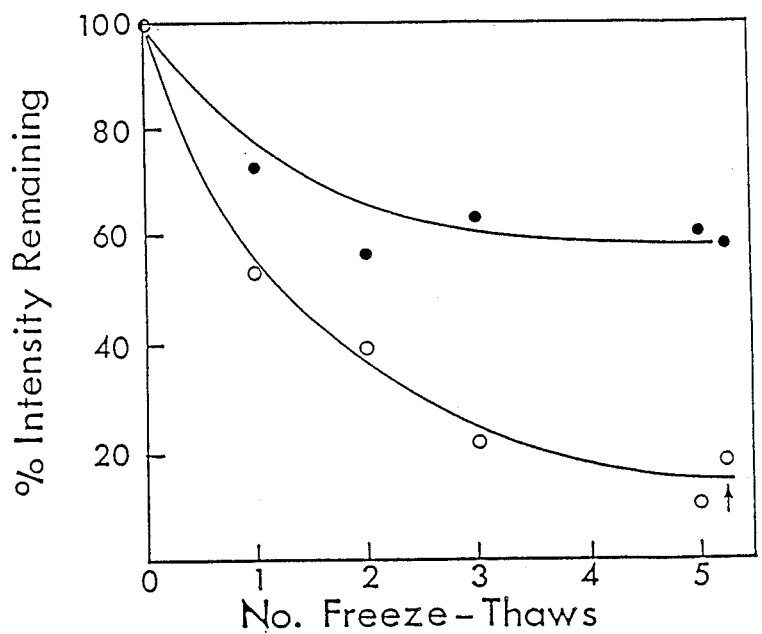
FIG. 2 is a graph showing the effect of the number of freeze-thaw cycles on the $^{31}P$ NMR signal intensity.

The influence of the number of liquid nitrogen 40° C. water constant temperature bath freeze-thaw cycles on the $^{31}$P NMR signal intensity of egg phosphatidylcholine multilamellar vesicles prepared in the presence of 0.5 mM $Mn^{2+}$ (●) or 5 mM $Mn^{2+}$ (○) are shown in FIG. 2. The samples were prepared using the materials and procedures of Example 1. The signal intensities were obtained by cutting and weighing the normalized spectra. The arrow indicates the signal intensity obtained after addition of sufficient aqueous Triton X-100 (10%, wt per vol) to solubilize the sample.

EXAMPLE 3

Figure 3:
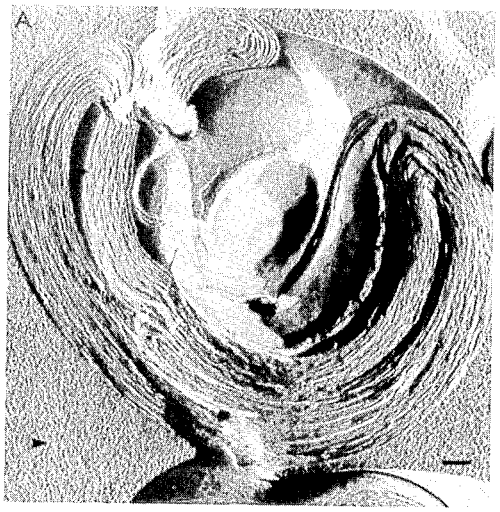
FIG. 3 is shows freeze fracture electron micrographs of (A) MLV's and (B) FATMLV's of the present invention.
Figure 3:
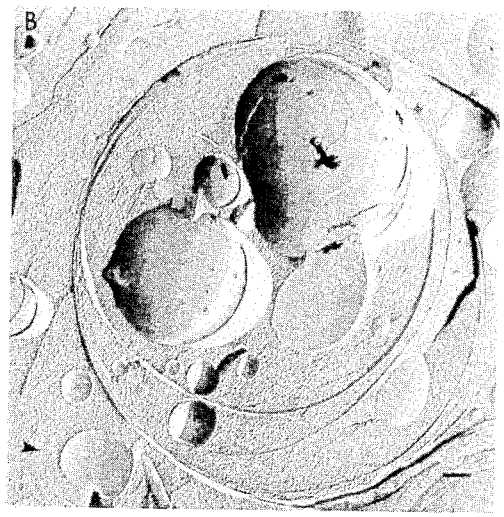

Freeze fracture electron micrographs of MLV's before (A) and after (B) five liquid nitrogen 40° C. water constant temperature bath freeze-thaw cycles are shown in FIG. 3. The phospholipid concentration was 100 mg/ml. The samples were prepared using the procedures and materials of Example 1. The arrow indicates the direction of shadowing and the bar represents 140 nm.

COMPARATIVE EXAMPLE 1

Two vesicle preparation procedures were employed. The first, as described in Example 1, entailed dispersion of dry egg phosphatidylcholine (PC) in 20 mM Hepes, 150 mM sodium chloride (pH 7.5) by vortex mixing followed by five freeze-thaw cycles employing liquid nitrogen and a 40° C. water constant temperature bath.

The second procedure was that of Westman et al., *Biochemica et Biophysica Acta*, 685, 315–328 (1982), which utilized egg PC dried down to a thin film on the walls of a glass test tube as the starting material. To the thin film was added a sufficient amount of an unbuffered 0.1M sodium chloride solution containing 0, 2 or 4 mg tetracaine/ml to yield a final lipid concentration of 50 mg/ml. The lipid is then dispersed by vortex mixing. The pH of the sample is then adjusted to 7.5 using sodium hydroxide or hydrochloric acid followed by five freeze-thaw cycles employing ethanol/dry ice and a 40° water constant temperature bath.

Trapped volumes and trapping efficiencies were determined by including $^{22}$Na+ (1 uCi/ml) in the aqueous phase in which the lipid was dispersed. After the multilamellar vesicles were formed, aliquots were assayed for lipid phosphorus and $^{22}$Na+ untrapped $^{22}$Na+ was removed by washing with $^{22}$Na+-free buffer employing low speed centrifugation. This procedure was repeated until supernatant counts were reduced to background levels. Aliquots of the pellet were then assayed for $^{22}$Na+ and lipid phosphorous. Trapping efficiencies were calculated as the ratio of the cpm per umol lipid after and before removal of untrapped $^{22}$Na+. Standard deviations, when given, were calculated from results obtained from 3 samples.

$^{31}$Phosphorus-NMR spectra were collected at 20° C. employing a Bruker WP200 spectrometer utilizing a 10 KHz sweep width, 2 sec interpulse delay and broad band proton decoupling. Peak intensities were obtained by cutting and weighing before and after addition of $MnCl_2$ in sufficient amounts to totally quench the externally exposed phospholipid signal.

Freeze-fracture replicas were prepared by mixing vesicle preparations (adjusted to 50 mg/ml) with glycerol (25% by volume), freezing samples in a freon slush and fracturing them employing a Balzers BAF 400D apparatus. Micrographs were obtained by using a Phillips 400 electron microscope.

Table 1 summarizes the trapped volume, trapping efficiency and $^{31}$P-NMR characteristics for MLV's and FATMLV's produced at varying concentrations by the procedures of the present invention and those produced by the Westman, et. al. procedure at 50 mg egg PC/ml in the presence of 0, 2 and 4 mg tetracaine/ml. Five freeze-thaw cycles employing liquid nitrogen dramatically increases the trapped volume and corresponding trapping efficiency of FATMLV preparations as compared to the non-freeze-thawed counterpart. This trapped volume increase is greater than 10-fold for FATMLVs prepared at 50 and 100 mg egg PC/ml while FATMLV's prepared st 200 and 400 mg egg PC/ml exhibit increases of 6.5- and 3.7-fold, respectively. The less dramatic trapped volume increases observed for FATMLV systems prepare at 200 and 400 mg egg PC/ml are likely due to the limited availability of aqueous phase where 76.7 and 88.6% of the sample volume, respectively, is contained within the FATMLVs. The freeze-thaw protocol employed by Westman et al. also increases the trapped volume of FATMLVs but not to the extent observed for our systems (1.92, 2.23 and 3.44 ul/umol egg PC in the presence of 0, 2 and 4 mg tetracaine/ml, respectively, compared with 5.02 ul/umol egg PC with our preparation).

Table 1 also demonstrates that the trapping efficiencies of MLV's and Westman FATMLV's are significantly lower than those observed for FATMLV's of the present invention.

$^{31}$P-NMR and freeze-fracture electron microscopy results corroborate the relationship of trapped volumes amoung the various vesicle preparations. The proportion of lipid in the outermost bilayer of vesicles can be determined by multiplying the percent $^{31}$P-NMR signal removed with $Mn^{2+}$ addition by a factor of 2. As demonstrated in FIG. 4, FATMLV's produced by our procedure contain approximately 33% of the lipid in the outermost bilayer, a factor of 2 and 3 greater than Westman FATMLV's and standard MLVs, respectively. This result indicates that MLVs and Westman vesicles contain more lamellae per vesicle than do FATMLV's of the present invention produced at 50 mg/ml and is consistent with the lower trapped volumes observed for the prior systems.

In summary, the FATMLVs produced according to the Westman procedure and FATMLVs prepared by our protocol exhibit three major differences in physical characteristics. First, ours exhibit a 1.4- to 2.2-fold greater trapped volume than Westman's. Second, our FATMLVs display greater trapping efficiencies than do Westman's when prepared at 50 mg egg PC/ml and trapping efficiencies approaching 90% can be achieved by increasing the lipid concentration. Third, our FATMLVs contain approximately 2-fold more lipid in the outermost bilayer than do Westman's.

COMPARATIVE EXAMPLE 2

Results were compared using liquid nitrogen and dry ice/ethanol (ETOH) in the freezing and thawing of multilamellar vesicles.

Egg PC MLV's were prepared at a concentration of 50 mg/ml in 20 mM Hepes, 150 mM NaCl (pH 7.5) by vortex mixing for approximately 5 min. in the presence of $^3$H-inulin as an aqueous marker. In the cases where lipid was used as a film, 50 mg egg PC was dissolved in 0.25 ml chloroform, the chloroform was removed with a stream of nitrogen and residual solvent was removed by high vacuum. The MLV's were subsequently frozen and thawed five times employing either a dry ice/ethanol bath or liquid nitrogen as indicated and a 400C. water constant temperature bath. Aliquots were then taken and analyzed for lipid-phosphorus and radioactivity. Free (unentrapped) $^3$H-inulin was removed by washing the vesicles employing low speed centrifugation until supernatant counts were reduced to background levels. Aliquots were again taken and analyzed for lipid phosphorus and radioactivity. Trapping efficiencies were calculated as the dpm/umol egg PC after removal of free inulin divided by the dpm/umol egg PC obtained before the washing procedure. Results are shown in Table 2.

EXAMPLE 4

Figure 4:
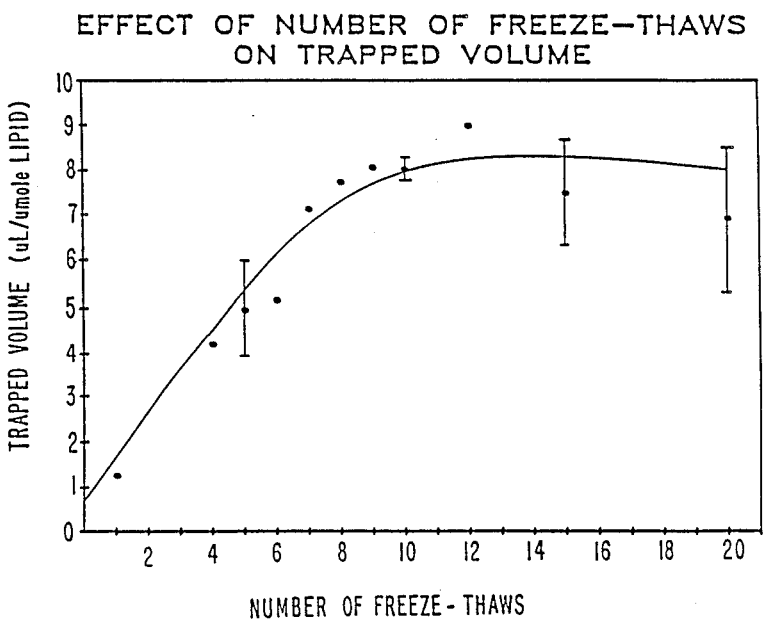
FIG. 4 is a graph showing the effect of the number of freeze-thaw cycles on trapped volume.

FIG. 4 shows the effects of the number of freeze-thaw cycles on the trapped volume of FATMLV's of the present invention. MLV's were prepared from powdered egg PC in 20 mM Hepes, 150 mM sodium chloride (ph 7.5) as described in Example 1. The samples were frozen and thawed the indicated number of times employing liquid nitrogen and a 40° C. water constant temperature bath. The samples (50 mg egg PC/ml) were assayed for lipid phosphous and radioactivity before and after removal of unentrapped $^3$H-inulin as described in Comparative Example 2. Vesicle trapped volume increased dramatically between zero and eight freeze thaw cycles from 0.5 to 8 ul/m mole egg PC, respectively. Increasing the number of freeze-thaw cycles from 8 to 20 resulted in no significant increase in FATMLV trapped volume.

EXAMPLE 5

Figure 5:
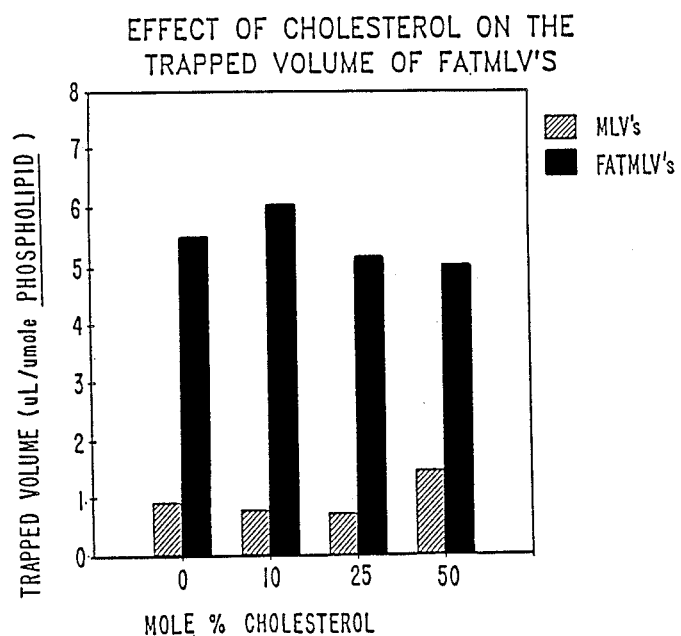
FIG. 5 is a graph showing the effect of cholesterol on the trapped volume of FATMLV's of the present invention.

FIG. 5 shows the effect of cholesterol content on the trapped volume of FATMLV's of the present invention. Varying amounts of egg PC and cholesterol as indicated in FIG. 6 were dissolved in 0.5 ml chloroform and dried to a thin film on the walls of glass test tubes utilizing a stream of nitrogen and high vacuum. When no cholesterol was present, the concentration of egg PC was 50 mg/ml. MLV's were then prepared in the presences of 20 mM Hepes, 150 mM sodium chloride (pH 7.5) containing $^3$H-inulin as described in Example 1. FATMLV's were produced by freeze thawing the MLV's five times employing liquid nitrogen and a 40° C. constant temperature bath. Removal of unentrapped $^3$H-inulin and determination of vesicle trapped volumes were accomplished as described in Comparative Example 2.

EXAMPLE 6

FATMLV's using tobramycin phosphate (100 mg/ml), egg PC (300 mg/ml), at a pH of less than 3, preferably between 2 and 3, resulted in a 43.1% trapping efficiency. Trapping efficiencies can be increased by reducing the tobramycin phosphate concentration. Tobramycin does not act as an ideal aqueous marker because tobramycin interacts with the PC headgroup. The procedures of Example 1 were employed. An aqueous solution (1 ml of tobramycin adjusted to a pH of 2.0 with phosphoric acid was added to 300 mg of egg PC and dispersed with vortexing. The samples were freeze-thawed five times; sized to 400 nm with five passes through two stacked 400 nm pore-sized polycarbonate filters at a pressure of 200 p.s.i., freeze-thawed an additional two times and extruded an additional five times through two stacked polycarbonate filters having a 400 nm pore size. A sized tobramycin-liposome composition resulted.

EXAMPLE 7

FATMLV's were prepared from egg PC (400 mg/ml), pilocarpine hydrochloride (40 mg/ml, pH=4.1) according to the procedure of Example 1. The FATMLV had a trapping efficiency of 88.6 percent and a trapped volume of 1.77 ul/umol phospholipid. Homogeneously sized vesicles were prepared by extruding the FATMLV ten times through two stacked polycarbonate filters with a 50 nm pore size. Sized pilocarpine-containing vesicles resulted.

TABLE 1
Physical Characteristics of MLV's, Westman FATMLV's and FATMLV's of the Present Invention

| Sample | Lipid Concentration (mg/ml) | Trapped Volume (ul/umol lipid) | Trapping Efficiency (%) | % $^{31}P$ NMR Signal Removed with $Mn^{2+}$ |
|---|---|---|---|---|
| MLV | 100 | 0.47 0.03 | 5.8 | 5.0 |
| Westman FATMLV (0 mg tetracaine) | 50 | 1.92 0.5 | 12.0 | 14.0 |
| Westman FATMLV (2 mg tetracaine) | 50 | 2.23 | 13.9 | 18.5 |
| Westman FATMLV (4 mg tetracaine) | 50 | 3.44 | 21.5 | 18.8 |
| FATMLV | 50 | 5.02 ± 0.04 | 31.3 | 16.6 |
| FATMLV | 100 | 5.27 ± 0.17 | 65.9 | 14.7 |
| FATMLV | 200 | 3.07 ± 0.05 | 76.7 | 7.4 |
| FATMLV | 400 | 1.77 ± 0.09 | 88.6 | 7.2 |

TABLE 2

| Sample | Freezing Media | Trapped Volume (ul/umol EPC) | Trapping Efficiency (%) |
|---|---|---|---|
| EPC (powder) | dry ice/ETOH | 3.44 | 21.5 |
| EPC (film) | dry ice/ETOH | 3.62 | 22.6 |
| EPC (powder) | liquid nitrogen | 6.81 | 42.5 |
| EPC (film) | liquid nitrogen | 5.54 | 34.6 |

TABLE 3
Size Distributions of Extruded Vesicles[a]

| Filter pore size (nm) | Mean Diameter ± S.D. (nm) | |
|---|---|---|
| | Freeze-fracture electron microscopy[b] | Quasielastic light scattering[c] |
| 400 | 243 ± 91 | N.D.[d] |
| 200 | 151 ± 36 | 179.9 ± 55 |
| 100 | 103 ± 20 | 138.7 ± 36 |
| 50 | 68 ± 19 | 73.8 ± 18 |
| 30 | 56 ± 17 | 63.1 ± 17 |

[a]MLV's (100 mg EPC/ml) were frozen and thawed 5 times prior to the extrusion process. These FATMLV's were then passed 20 times through 2 (stacked) polycarbonate filters of the indicated pore size.
[b]Size distribution analysis of vesicle employing freeze-fracture electron microscopy were completed as described in Materials and Methods. Mean diameters and S.D. were determined by measuring >150 vesicles.
[c]Size distribution analysis of vesicles employing quasielastic light scattering were completed as described in Materials and Methods.
[d]Statistical analysis of the data yielding low fit error could not be accomplished. A mean vesicle diameter value is therefore not reported.

What is claimed is:

1. A multilamellar vesicle having interlamellar equal solute distribution, containing a water soluble bioactive agent dispersed in an aqueous phase comprising an aqueous medium, a lipid concentration of at least about 50 mg/ml and a trapping efficiency of greater than about 40 percent.

2. The vesicle of claim 1 wherein the lipid concentration is at least about 100 mg/ml and the trapping efficiency is at least about 50 percent.

3. The vesicle of claim 2 wherein the lipid concentration is between about 100 and 1000 mg/ml.

4. The vesicle of claim 3 wherein the lipid concentration is between about 100 and 400 mg/ml.

5. The vesicle of claim 1 having an outer bilayer comprising less than about 35% of the total lipid contained in the vesicle.

6. The vesicle of claim 1 wherein the aqueous medium comprises an aqueous buffer.

7. The vesicle of claim 1 wherein the lipid comprises phospholipid.

8. The vesicle of claim 7 wherein the phospholipid comprises phosphatidylcholine.

9. The vesicle of claim 7 wherein the lipid additionally comprises a sterol.

10. The vesicle of claim 9 wherein the sterol is cholesterol.

11. A multilamellar vesicle having interlamellar equal solute distribution dispersed in an aqueous phase comprising an aqueous medium, a lipid concentration of at least about 50 mg/ml and a trapping efficiency of at least about 40 percent which is prepared in the absence of organic solvent or detergents by a method comprising the steps of:
 (a) dispersing a lipid in an aqueous solvent to form a multilamellar vesicle;
 (b) rapidly freezing the multilamellar vesicle at about −70° C. to obtain a frozen lipid-aqueous medium mixture;
 (c) warming the mixture in a constant temperature bath to melt the aqueous medium; and
 (d) repeating steps (b) and (c) at least about three times.

12. The vesicle of claim 11 wherein the mixture is rapidly frozen in liquid nitrogen.

13. The vesicle of claim 11 wherein the lipid concentration is at least about 100 mg/ml and the trapping efficiency is at least about 50 percent.

14. The vesicle of claim 11 wherein the lipid concentration is between about 100 and 1000 mg/ml.

15. The vesicle of claim 11 wherein the lipid concentration is between about 100 and 400 mg/ml.

16. The vesicle of claim 11 wherein the lipid comprises phospholipid.

17. The vesicle of claim 16 wherein the phospholipid comprises phosphatidylcholine.

18. The vesicles of claim 16 wherein the lipid additionally comprises a sterol.

19. The vesicle of claim 18 wherein the sterol is cholesterol.

20. The vesicle of claim 11 which is prepared by the additional step of filtering the multilamellar vesicle dispersion under pressure through a polycarbonate filter having a pore size of about 200 nanometers to about 400 nanometers.

21. A process for preparing a multilamellar vesicle having interlamellar equal solute distribution, dispersed in an aqueous phase in the absence of organic solvent or detergents comprising the steps of:
 (a) dispersing a lipid in an aqueous solvent to form a multilamellar vesicle;

(b) rapidly freezing the multilamellar vesicle at about −70° C. to obtain a frozen lipid-aqueous medium mixture;

(c) warming the mixture in a constant temperature bath to melt the aqueous medium; and (d) repeating steps (b) and (c) at least about three times.

22. The process of claim 21 wherein liquid nitrogen is employed in Step (b).

23. The process of claim 21 comprising the additional step of concentrating the multilamellar vesicle dispersion.

24. The process of claim 21 comprising the additional step of filtering the multilamellar vesicle dispersion through a polycarbonate filter.

25. A multilamellar vesicle having interlamellar equal solute distribution, having a captured volume of at least about 1.77 ul/umol lipid, and having non-concentric bilayers.

26. The multilamellar vesicle of claim 25 additionally comprising a bioactive agent.

27. The multilamellar vesicle of claim 26 wherein the bioactive agent in hydrophilic.

28. The multilamellar vesicle of claim 26 wherein the bioactive agent is lipophilic.

* * * * *

UNITED STATES PATENT AND TRADEMARK OFFICE
CERTIFICATE OF CORRECTION

PATENT NO.   : 4,975,282
DATED        : December 4, 1990
INVENTOR(S)  : Pieter R. Cullis et al It is certified that error appears in the above-identified patent and that said Letters Patent is hereby corrected as shown below:

Col. 14, line 35, claim 11, step (b), replace "-70°C" with -- -196°C --.

Col. 15, line 2, claim 21, step (b), replace "-70°C" with -- -196°C --.

Signed and Sealed this

Fourteenth Day of July, 1992

Attest:

DOUGLAS B. COMER

*Attesting Officer*    *Acting Commissioner of Patents and Trademarks*